US009538968B2

(12) United States Patent
Rotondo et al.

(10) Patent No.: US 9,538,968 B2
(45) Date of Patent: Jan. 10, 2017

(54) APPARATUS AND METHOD FOR DIGITAL RADIOGRAPHY

(71) Applicants: Giuseppe Rotondo, Pantigliate (IT); Fabio Lissandrello, Milan (IT); Claudio Giani, Busto Arsizio (IT)

(72) Inventors: Giuseppe Rotondo, Pantigliate (IT); Fabio Lissandrello, Milan (IT); Claudio Giani, Busto Arsizio (IT)

(73) Assignee: DE GOTZEN S.R.L., Olgiate Olona (Varese) (IT)

( * ) Notice: Subject to any disclaimer, the term of this patent is extended or adjusted under 35 U.S.C. 154(b) by 258 days.

(21) Appl. No.: 14/371,010

(22) PCT Filed: Jan. 22, 2013

(86) PCT No.: PCT/EP2013/051147
§ 371 (c)(1),
(2) Date: Jul. 8, 2014

(87) PCT Pub. No.: WO2013/110611
PCT Pub. Date: Aug. 1, 2013

(65) Prior Publication Data
US 2015/0010126 A1    Jan. 8, 2015

(30) Foreign Application Priority Data

Jan. 27, 2012 (IT) .............................. MI2012A0099

(51) Int. Cl.
*A61B 6/00* (2006.01)
*A61B 6/03* (2006.01)
*A61B 6/06* (2006.01)
*A61B 6/14* (2006.01)

(52) U.S. Cl.
CPC ............. *A61B 6/4078* (2013.01); *A61B 6/032* (2013.01); *A61B 6/06* (2013.01); *A61B 6/14* (2013.01);

(Continued)

(58) Field of Classification Search
CPC ............. A61B 6/06; A61B 6/14; A61B 6/032; A61B 6/4035; A61B 6/4078; A61B 6/4266; A61B 6/4283; A61B 6/4291; A61B 6/4417; A61B 6/501; A61B 6/4441; A61B 6/4233; A61B 6/469; A61B 6/588; A61B 6/5223; A61B 6/4429
See application file for complete search history.

(56) References Cited

U.S. PATENT DOCUMENTS 5,511,106 A    4/1996 Doebert et al.
6,055,292 A    4/2000 Zeller et al.
(Continued)

FOREIGN PATENT DOCUMENTS

EP    1 752 099    2/2007
EP    1 752 100    2/2007
(Continued)

OTHER PUBLICATIONS

International Search Report dated Apr. 3, 2013, corresponding to PCT/EP2013/051147.

*Primary Examiner* — Hoon Song
(74) *Attorney, Agent, or Firm* — Young & Thompson (57) ABSTRACT

An X-ray apparatus for digital radiography has a rotating arm where the X-ray source and X-ray sensor cassette are oppositely mounted. The source has a primary collimator to adjust the X-ray beam size according to the selected imaging modality. The sensor cassette encloses a first X-ray detector for a first imaging mode, while a second X-ray detector usable for a second imaging mode is detachably mounted on the external side of the sensor cassette. The sensor cassette accommodates a second collimator to create a fan shaped X-ray beam for a third imaging modality. The sensor cassette has a linear motorized movement which is used for: aligning the X-ray beam with respect to the first and second (Continued)

detector; positioning the first detector in the first imaging mode to achieve an extended view; and scanning movement during the third imaging modality synchronized with the horizontal movement of a third X-ray detector.

11 Claims, 4 Drawing Sheets

(52) U.S. Cl.
CPC ............ *A61B 6/4417* (2013.01); *A61B 6/4035* (2013.01); *A61B 6/4266* (2013.01); *A61B 6/4291* (2013.01)

(56) References Cited

U.S. PATENT DOCUMENTS

| | | |
|---|---|---|
| 6,118,842 A | 9/2000 | Arai et al. |
| 7,103,141 B2 | 9/2006 | Sonobe et al. |
| 7,236,563 B2 | 6/2007 | Sa et al. |
| 7,315,608 B2 | 1/2008 | Sa et al. |
| 7,559,692 B2 | 7/2009 | Beckhaus et al. |
| 7,783,002 B2 | 8/2010 | Savinen et al. |
| 7,798,708 B2 | 9/2010 | Erhardt et al. |
| 8,300,762 B2 | 10/2012 | Suzuki et al. |
| 2007/0030950 A1 | 2/2007 | Sa et al. |
| 2007/0030952 A1 | 2/2007 | Sa et al. |
| 2009/0168966 A1* | 7/2009 | Suzuki ............ A61B 6/032 378/116 |
| 2010/0246755 A1 | 9/2010 | Suzuki et al. |

FOREIGN PATENT DOCUMENTS

| | | |
|---|---|---|
| EP | 2 198 783 | 6/2010 |
| EP | 2 210 559 | 7/2010 |
| WO | 2010/128404 | 11/2010 |

* cited by examiner

APPARATUS AND METHOD FOR DIGITAL RADIOGRAPHY

FIELD OF THE INVENTION

The invention relates to a method for Digital Radiography by means of a combined multi-sensor X-ray imaging apparatus, capable of performing according to multiple imaging modes, the method comprising the steps of:

- Positioning an object in between a radiation source and a x-ray detector using an object support and positioning system;
- Selecting a radiographic imaging modality and a desired region of interest;
- Adjusting, by one or more x-ray collimators, the shape of the x-ray beam according to the selected imaging modality;
- Positioning the X-ray detector in a predefined position into the X-ray beam;
- Generating X-ray radiation by the radiation source;
- Performing a movement for scanning of the object while detecting the X-ray radiation by means of the x-ray detector;
- Performing a readout of the x-ray detector image data, acquisition and elaboration in order to obtain a processed image or tridimensional data set of the selected region of interest according to the selected imaging mode.

The invention further relates to an apparatus arranged for performing the method.

BACKGROUND OF THE INVENTION

Combined X-ray imaging apparatuses, capable of performing according to multiple imaging modes, are well known in the state of the art.

A dual purpose X-ray imaging apparatus equipped with a single sensor and capable of multiple imaging modes, namely partial CT (computerized tomography) imaging additional to panoramic imaging, for use in dental and medical diagnosis, is known from U.S. Pat. No. 6,118,842.

Another apparatus providing at least one x-ray detector which can be positioned in multiple imaging positions, and accordingly exposed by a collimated x-ray beam, depending on a selected imaging mode, is known from U.S. Pat. No. 6,055,292. The embodiment of a single movable case containing two x-ray detectors which can be positioned depending on imaging mode is further known from U.S. Pat. No. 7,559,692 and U.S. Pat. No. 7,798,708.

EP 1752099 teaches about a combined panoramic and computed tomographic apparatus characterized by a X-ray sensor part equipped with dual X-ray detectors and rotatable around an eccentric axis, so that, depending on the selected imaging mode, a different X-ray detector is placed in the X-ray beam at a preferred distance from the source and is exposed to radiation.

EP 1752100 teaches about a combined panoramic and computed tomographic apparatus characterized by a X-ray sensor part equipped with dual X-ray detector mounts on the rotating arm, displaced at different distance from the source. The X-ray detector mount for panoramic imaging is located closer to the source and can slide out of the beam when CT imaging mode is selected.

EP 1752099 teaches about a combined panoramic, computed tomography and cephalometric apparatus characterized by a X-ray sensor part equipped with dual X-ray detectors either rotatable around an axis, or displaceable by sliding, so that, depending on the selected imaging mode, a different X-ray detector is placed in the X-ray beam at a preferred distance from the source and is exposed to radiation.

U.S. Pat. No. 7,783,002 teaches about a combined panoramic and computed tomographic apparatus characterized by a fixed CT X-ray detector and a movable panoramic X-ray detector having a pivoting movement to turn it out of the beam when CT imaging mode is selected.

WO 2010/128404 teaches about a combined panoramic, computed tomography and cephalometric apparatus having an extended rotary arm and providing various arrangements for detector positioning in and out of the x-ray beam at predefined distances from the source, either by translation of a movable platen, or by rotation around a pivot axis, including a third position where both a panoramic and a CT detector are out of beam and a third detector for cephalography is exposed.

Concerning the cephalometric imaging mode U.S. Pat. No. 5,511,106 teaches a method of scanning the patient skull by a secondary collimator located in proximity of the patient and translating with a linear movement synchronized with the movement of the detector.

U.S. Pat. No. 7,103,141 teaches a method of modulating the radiation intensity during the cephalometric scanning process, either by adjustment of the tube voltage, or the tube current, or the scanning speed.

US 2009/168966 teaches about a combined apparatus having multiple imaging modes, to among which computed tomography, where the irradiation field is changed according to the selected imaging mode by a primary and secondary collimation mechanism; in particular, various collimator arrangements are described where the secondary collimator is essentially mentioned for proximal limitation in front of the CT detector and it is not disclosed a movable secondary collimation for cephalographic scanning placed in an X-ray sensor cassette posterior to the detector with respect to the source.

EP 1752099 teaches about a combined apparatus for panoramic and CT imaging modes, having adjustable magnification ratio and about a mounting part for attaching and detaching the suitable X-ray detector; however, it does not disclose cephalographic imaging and secondary collimation for cephalography.

EP 2198783 teaches about a simplified x-ray apparatus having a fixed secondary collimator placed at the extremity of a rotating arm, utilized for X-ray scanning in cephalography by a roto-translation movement of the same rotating arm and does not teach about a method for X-ray scanning in cephalography where the rotating arm is steady and the secondary collimator is moved thanks to the translational movement of the detector cassette where said secondary collimator is located in a position posterior to the detector with respect to the source.

Concerning the cone beam CT image acquisition and reconstruction various publication teach the method and algorithms, among which:

Med Phys. 2003 October; 30(10):2758-61.

Liu V, Lariviere N R, Wang G.—CT/Micro-CT Lab, Department of Radiology, University of Iowa, Iowa City, Iowa 52242, USA.

X-ray micro-CT with a displaced detector array: application to helical cone-beam reconstruction. In x-ray micro-CT applications, it is useful to increase the field of view by offsetting a two-dimensional (2D) detector array. In this technical note, we briefly review the methods for image reconstruction with an asymmetric 2D detector array, elaborate on the use of an associated weighting scheme in the case of helical/spiral cone-beam scanning, and perform a series of numerical tests to demonstrate helical cone-beam image reconstruction with such an arrangement.

Med Phys. 2002 July; 29(7):1634-6.—Wang G.—Department of Radiology, University of Iowa, Iowa City 52242, USA. ge-wang@uiowa.edu X-ray micro-CT with a displaced detector array.

Because the sizes of samples differ in x-ray micro-CT applications, it is desirable to have a mechanism to change the field of view of a micro-CT scanner. A well-known way to double the diameter of the field of view is to displace a detector array by 50%. In this paper, we propose to displace a detector array by an amount of greater than 0% but less than 50% for a continuously adjustable field of view, and formulate a weighting scheme for artifact-free reconstruction. Then, we perform numerical simulation with the Shepp-Logan phantom to demonstrate the feasibility in fan-beam and cone-beam geometry.

Yu, L. Pelizzari, C. Pan, X. Riem, H. Munro, P. Kaissl, W.—Dept. of Radiol., Chicago Univ., Ill., USA This paper appears in: Nuclear Science Symposium Conference Record, 2004 IEEE Publication Date: 16-22 Oct. 2004 Volume: 5—On page(s): 3249-3252 Vol. 5

ISSN: 1082-3654
E-ISBN: 0-7803-8701-5
Print ISBN: 0-7803-8700-7
INSPEC Accession Number: 8588605
Digital Object Identifier: 10.1109/NSSMIC.2004.1466376
Current Version Published: 1 Aug. 2005
Abstract In many implementations of cone-beam CT in radiotherapy for target positioning, it is not uncommon that the maximum allowable field of view (FOV) cannot cover the patient because of the limited size of the flat-panel detector. In this situation, the measurements will contain truncated projections, leading to significant artifacts in reconstructed images. Asymmetric cone-beam configurations can be used for increasing the FOV size by displacing the detector panel to one side. From the data acquired with such an asymmetric configuration, the well-known algorithm developed by Feldkamp, Davis, and Kress (FDK) can be modified to reconstruct images. With increasing detector asymmetry, however, the modified FDK algorithm may produce significant aliasing artifacts. In this work, we develop a novel algorithm for image reconstruction in asymmetric cone-beam CT, which can generate images with improved numerical properties and allow for large detector asymmetry. We have employed the asymmetric configuration and the developed algorithm in a cone-beam CT system in radiotherapy to increase the FOV size. Preliminary phantom studies have been conducted to validate the asymmetric configuration and the proposed reconstruction algorithm.

Conebeam X-ray computed tomography with an offset detector array

Gregor, J.; Gleason, S. S.; Paulus, M. J.;
Dept. of Comput. Sci., Tennessee Univ., Knoxville, Tenn., USA This paper appears in: Image Processing, 2003. ICIP 2003. Proceedings. 2003
International Conference on
On page(s): II-803-6 vol. 3
ISSN: 1522-4880
Print ISBN: 0-7803-7750-8
INSPEC Accession Number: 7978666
Digital Object Identifier: 10.1109/ICIP.2003.1246802
Current Version Published: 24 Nov. 2003
Abstract Conventional X-ray computed tomography (CT) imaging is based on the assumption that the entire cross-section of an object is illuminated with X-rays at each view angle. When imaging a large object, a large detector array is thus needed. As an alternative, we propose to offset a normal sized detector array such that slightly more than one half of the required projection data is acquired. During reconstruction, the missing data is accounted for by means of an interpolation and weighting scheme. This algorithmic approach for extending the field of view, which we here present in the context of the popular Feldkamp algorithm, is simple but effective. Supportive experimental results are provided based on simulated phantom data as well as real data obtained from a MicroCAT™ which is a circular orbit microCT system for small animal imaging.

Comput Med Imaging Graph. 1996 January-February; 20(1):49-57.

Cone-beam CT from width-truncated projections.
Cho P S, Rudd A D, Johnson R H.
Source Department of Radiation Oncology, University of Washington School of Medicine, Seattle 98195-6043, USA.

Abstract

In this paper we report cone-beam CT techniques that permit reconstruction from width-truncated projections. These techniques are variants of Feldkamp's filtered backprojection algorithm and assume quasi-redundancy of ray integrals. Two methods are derived and compared. The first method involves the use of preconvolution weighting of the truncated data. The second technique performs post-convolution weighting preceded by non-zero estimation of the missing information. The algorithms were tested using the three-dimensional Shepp-Logan head phantom. The results indicate that given an appropriate amount of overscan, satisfactory reconstruction can be achieved. These techniques can be used to solve the problem of undersized detectors.

Phys Med Biol. 2005 Apr. 21; 50(8):1805-20. Epub 2005 Apr. 6.

Exact fan-beam image reconstruction algorithm for truncated projection data acquired from an asymmetric half-size detector.

Leng S, Zhuang T, Nett B E, Chen G H.
Source

Department of Medical Physics, University of Wisconsin-Madison, 53704, USA.

Abstract

In this paper, we present a new algorithm designed for a specific data truncation problem in fan-beam CT. We consider a scanning configuration in which the fan-beam projection data are acquired from an asymmetrically positioned half-sized detector. Namely, the asymmetric detector only covers one half of the scanning field of view. Thus, the acquired fan-beam projection data are truncated at every view angle. If an explicit data rebinning process is not invoked, this data acquisition configuration will reek havoc on many known fan-beam image reconstruction schemes including the standard filtered backprojection (FBP) algorithm and the super-short-scan FBP reconstruction algorithms. However, we demonstrate that a recently developed fan-beam image reconstruction algorithm which reconstructs an image via filtering a backprojection image of differentiated projection data (FBPD) survives the above fan-beam data truncation problem. Namely, we may exactly reconstruct the whole image object using the truncated to data acquired in a full scan mode (2 pi angular range). We may also exactly reconstruct a small region of interest (ROI) using the truncated projection data acquired in a short-scan mode (less than 2 pi angular range). The most important characteristic of the proposed reconstruction scheme is that an explicit data rebinning process is not introduced. Numerical simulations were conducted to validate the new reconstruction algorithm.

A first problem not resolved from the prior art is to provide a solution that is at the same time protecting the CT detector, which is usually highly expensive and should not be equipped with manual detachment possibility, but allowing manual detachment of the panoramic detector, which is typically an area sensor with elongated size, and can be conveniently displaced in a position for Cephalography so allowing execution of panoramic and cephalometric imaging modes with a single sensor.

A second problem not adequately resolved from the prior art is that in order to achieve a flexibility of operation and an economic mechanical and electrical solution, it is preferable to have an arrangement provided with a single movement capable of performing all the necessary detector positioning as well as the scanning movement required for Cephalography.

Among the necessary detector positioning is included the partial offset positioning required to perform a particular CT imaging mode defined in literature as "extended view", where thanks to the acquisition of multiple images by an offset rotation around the object an extended portion of the region of interest of the patient is reconstructed.

SUMMARY OF THE INVENTION

Proceeding from this related art, the present invention seeks to provide a method and an apparatus which avoids the drawbacks mentioned above by simplifying the construction and the geometry of the imaging system.

This object is achieved by an apparatus and method having the features of the independent claims. Advantageous embodiments and refinements are specified in claims dependent thereon.

The combined imaging apparatus of the invention is capable of performing x-ray imaging of objects, such as for example body parts, including more specifically the human skull and the oto-larynges districts, according to different imaging modalities.

In the preferred embodiment it is provided with a CT x-ray detector utilized for CT imaging, having a rectangular size, preferably in the range from 5×5 cm up to 13×13 cm and more.

It is also provided with a panoramic x-ray detector utilized for panoramic imaging, having an elongated imaging area, preferably in the range 6×150 mm.

It is furthermore provided with a cephalometric x-ray detector utilized for cephalometric imaging, having an elongated imaging area, preferably in the range 6×220 mm.

In a preferred configuration intended to improve the economy of the system the cephalometric x-ray detector can be conveniently utilized also for panoramic imaging, so reducing the ownership cost for the user. In such case the cephalometric x-ray detector can be displaced from panoramic to cephalometric position by a manually releasable connection.

According to the method, the CT detector is contained inside a metal and/or plastic enclosure, and is therefore protected and not accessible by the user. A secondary collimator is also mounted inside the same enclosure, located in a position adjacent to the CT sensor, and its aperture is so dimensioned in order to provide an emerging fan shaped x-ray beam exactly impinging on the cephalometric x-ray detector usually placed at a distance of about 1.5 m away from the x-ray source.

A panoramic detector is mounted on the outer side of the enclosure, also adjacently to the position of the secondary collimator, and is manually detachable by means of a mechanical and electrical release.

A cephalometric detector is mounted on a supporting structure located in a cephalometric position, at a distance typically around 1.5 m away from the x-ray source, and is also manually detachable by means of a mechanical and electrical release.

In a preferred configuration the cephalometric detector is manually detached from the cephalometric position and mounted in the panoramic position when panoramic imaging is required.

The CT detector enclosure, here following named the x-ray sensor cassette, is horizontally movable in a direction transverse to the central axis of the x-ray beam by means of a motor driven linear actuator.

In a first instance according to the method, the X-ray sensor cassette horizontal movement (25) is utilized to place the CT detector symmetrically horizontally aligned in the beam, when the CT imaging modality is chosen. Then the x-ray exposure and image acquisition process is started, by rotation of the rotary arm around the patient and simultaneous acquisition of multiple images according to a predefined sequence. In another instance according to the method, the X-ray sensor cassette horizontal movement (25) is utilized to place the CT detector asymmetrically horizontally aligned in the beam, namely partially offset respect to the central ray of the beam, as applicable when the "extended view" CT imaging modality is chosen. Then the x-ray exposure and image acquisition process is started, by rotation of the rotary arm around the patient and simultaneous acquisition of multiple images according to a predefined sequence. In such case the reconstruction algorithm will allow tridimensional reconstruction of an extended region of interest of the patient.

In another instance according to the method, the X-ray sensor cassette horizontal movement (25) is utilized to place the panoramic detector symmetrically horizontally aligned in the beam, when the panoramic imaging modality is chosen. Then the x-ray exposure and image acquisition process is started, by roto-translation of the rotary arm around the patient and simultaneous acquisition of multiple images according to a predefined sequence.

In another instance according to the method, the X-ray sensor cassette horizontal movement (25) is utilized to place the secondary x-ray collimator (24) in an extreme starting position for a cephalometric scanning, when the cephalometric imaging modality is chosen. Then the x-ray exposure scanning and image acquisition process is started, by synchronized linear translation of the X-ray sensor cassette carrying the secondary collimator (24) and of the cephalometric x-ray detector (9), and simultaneous acquisition of multiple images according to a predefined sequence.

In such process the primary x-ray collimator (22) is fixed with a wide aperture, and the secondary x-ray collimator (24) is moved by the same movement of the X-ray sensor cassette (23), in a way synchronized with the movement of the cephalometric X-ray detector (9), so generating a moving fan shaped X-ray beam impinging on the active area of the linear shaped cephalometric X-ray detector (9) during its horizontal translation. In this way the same motor drive utilized for the CT and panoramic sensor positioning is advantageously utilized for the extended view imaging process and for the cephalometric scanning process.

The movable X-ray sensor cassette carrying the secondary x-ray collimator (24) placed on the rotating arm therefore provides a simplified and economic construction of particular advantage in x-ray imaging modalities such as CT imaging, panoramic imaging and cephalometric imaging.

Additionally, means may be used for modulating the intensity of the beam during the panoramic or cephalometric scanning process. Such means may include among others modulation of tube voltage, or modulation of tube current, or variation of the scanning speed.

For example, in cephalometric imaging the intensity may be increased during the transition from a soft tissue area, such as the tip of the nose, to the bony area of a patient skull; in panoramic imaging the intensity may be increased during the transition from the spine of the patient.

The modulation can be according to a predefined profile, or according to a profile adjusted in response to a choice of the operator, or a particular morphological aspect of the patient. For example in cephalometric imaging the modulation can be performed in response to a measured dimension of a distance between the nasion and the acustic meatus of the patient.

The measurement of those morphological aspects can be done in a variety of ways, among which for example by acquisition of an electric signal from a length transducer, or by measurement on an acquired video image of the patient.

Of course when the modulation is performed automatically in response to a morphological aspect of the patient, the reliability of the process and the workload of the operator can be optimized.

In a further embodiment, the modulation can also be advantageously performed automatically in real time, in response to a feedback signal proportional to the actual or integrated dose measured in X-ray detector areas that correspond to the actual exposed regions of the patient. It can also follow a predefined profile of intensity, which is conveniently adjusted in response to the dose feedback signal.

BRIEF DESCRIPTION OF THE DRAWINGS

Further advantages and properties of the present invention are disclosed in the following description, in which exemplary embodiments of the present invention are explained in detail based on the drawings.

DETAILED DESCRIPTION OF THE INVENTION

According to a preferred embodiment, the imaging system of the present invention is based on a combined diagnostic x-ray system for panoramic, CT (Computed Tomography) and cephalometric examinations of the human skull.

Figure 1:
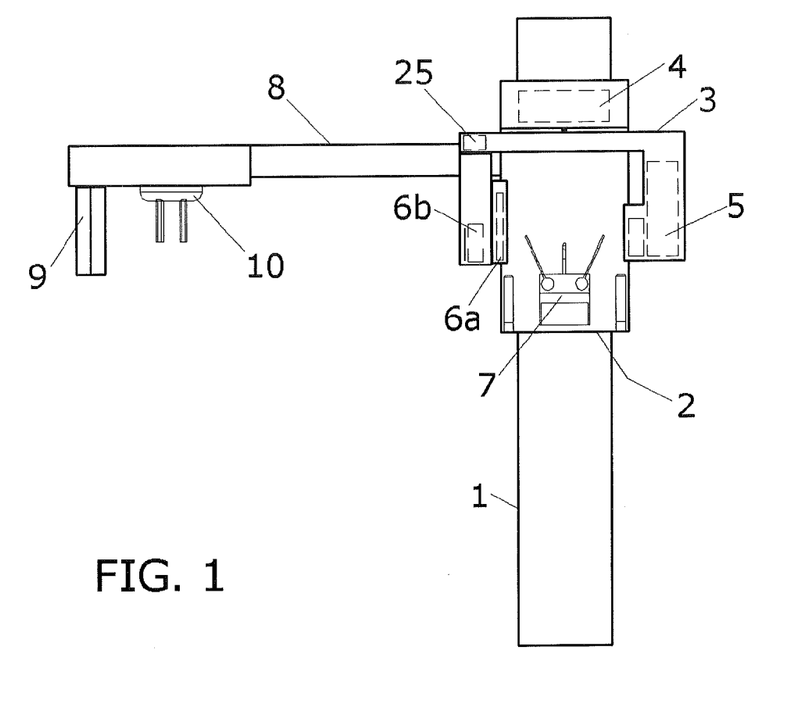
FIG. 1 is a front view of the imaging system.

Such apparatus is described in FIG. 1, where a column (1) supports vertically a sliding carriage (2) capable of vertical sliding along the column to adjust for a patient height.

The carriage (2) supports a rotating arm (3), by a cinematic unit (4) capable of driving the same rotating arm (3) according to rotational and translational movements.

The rotating arm (3) holds a x-ray generator (5) opposite to a panoramic x-ray detector (6a) and a CT x-ray detector (6b).

For panoramic and CT imaging, the patient is positioned below the rotating arm (3), in between the x-ray generator (5) and the x-ray detectors (6a) and (6b), supported and aligned by the patient positioning system (7).

The carriage (2) also holds a lateral arm (8) utilized for cephalometric imaging.

The lateral arm (8) holds a cephalometric x-ray detector (9) and a cephalometric patient positioning system (10).

For cephalometric imaging, the patient is positioned on a lateral side, at extended distance from the x-ray generator (5) and closer to the x-ray detector (9), supported and aligned by the patient positioning system (10).

For economic convenience the panoramic x-ray detector (6a) is detachable and can be manually displaced by the operator in the position of the cephalometric x-ray detector (9).

Figure 2:
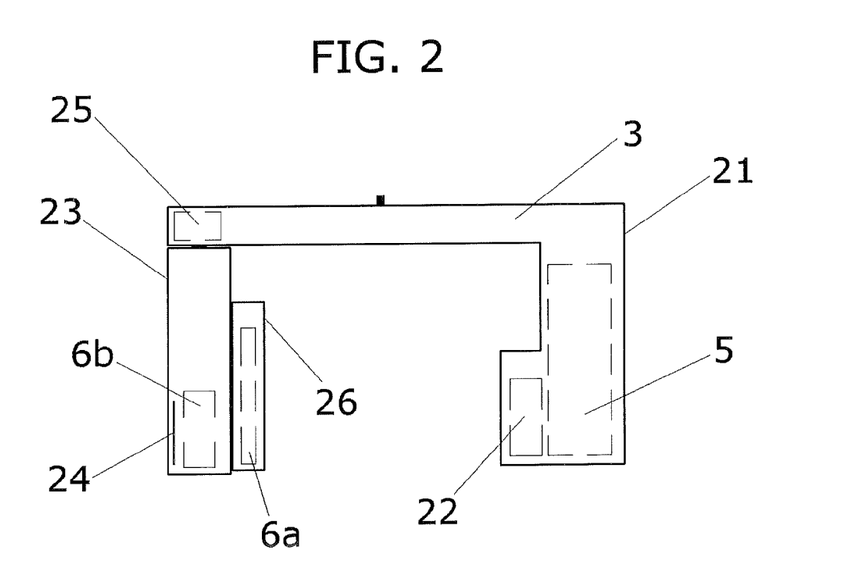
FIG. 2 is a view of the rotating arm supporting a x-ray generator and a x-ray sensor cassette.

With reference to FIG. 2, the details of the rotating arm (3) are shown.

The x-ray generator (5) is not accessible to the user, contained in a plastic or metal enclosure (21), and is provided with a primary x-ray collimator (22) which limits and shapes the x-ray beam according to the selected imaging modality.

On the opposite side the CT x-ray detector (6b) is contained within an enclosure defined as the x-ray sensor cassette (23), which is also containing a secondary collimator (24).

Externally of the x-ray sensor cassette (23), the panoramic x-ray detector (6a) is shown.

It is provided with its own enclosure (26), which is detachably mounted on the outer part of the same x-ray sensor cassette (23).

A motor drive (25) allows the horizontal movement of the x-ray sensor cassette (23), in a direction transverse to the x-ray beam.

Figure 3:
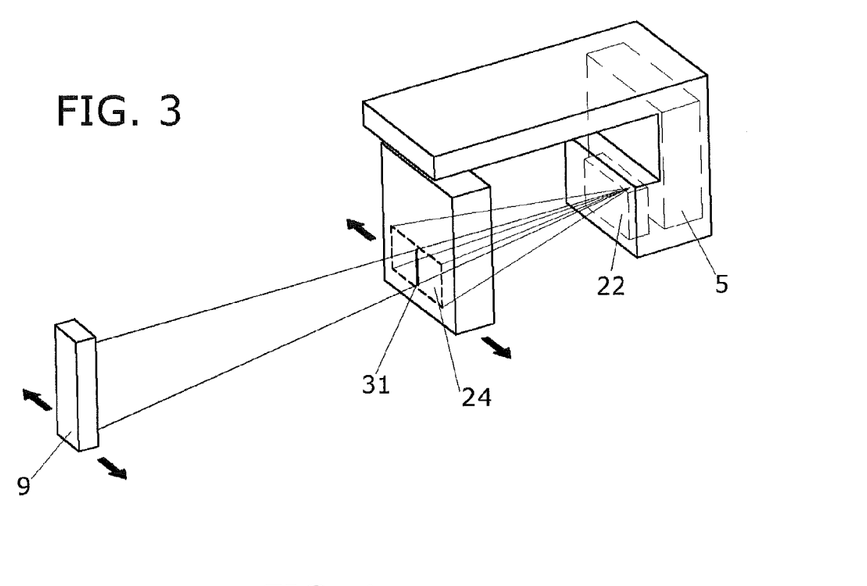
FIG. 3 is an assonometric view of the secondary collimator.

With reference to FIG. 3, the details of the secondary collimator (24) are illustrated.

The secondary collimator (24) is constituted by a lead sheet provided with an elongated aperture (31), allowing resizing of the x-ray beam emerging from the primary x-ray collimator (22) into a fan shaped x-ray beam of a width and height such that it will exactly impinge onto the active area of the cephalometric x-ray detector (9) during a cephalometric imaging procedure.

Figure 4:
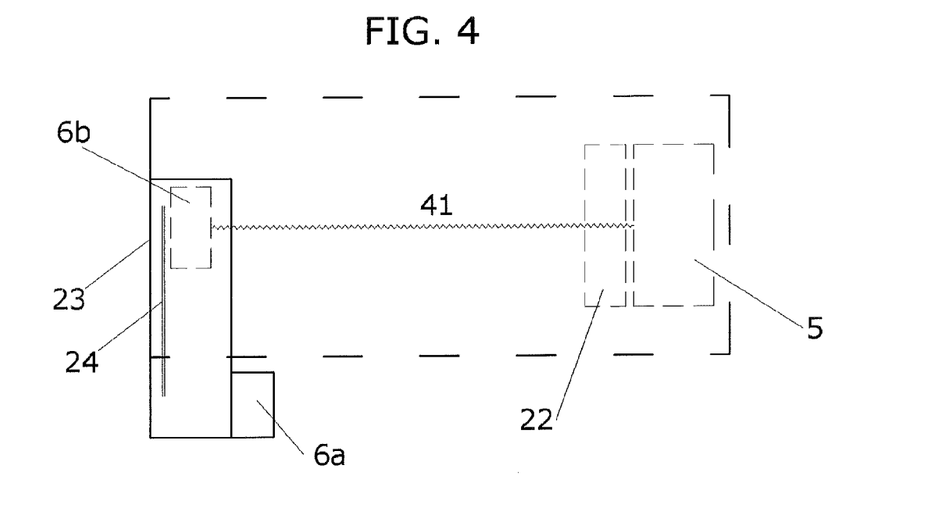
FIG. 4 is a top plan view showing the details of the CT imaging process.

With reference to FIG. 4, the details of the CT imaging process are illustrated.

When a CT imaging mode and a desired region of interest have been selected, the x-ray sensor cassette (23) is laterally slided by the horizontal motor drive (25), so that the CT x-ray detector (6b) is set in position for CT imaging, symmetrically aligned in the horizontal direction with respect to the central axis (41) of the x-ray beam. The primary x-ray collimator (22) aperture is so adjusted that the x-ray beam is rectangular shaped, having a width and height such as to exactly impinge on the active area of the CT x-ray detector (6b).

The patient is accurately positioned in between the x-ray generator (5) and the x-ray detector (6b), stabilized and aligned by the patient positioning system (7).

Under above conditions the rotating arm (3) starts a rotation around the patient, while simultaneously the x-ray generator (5) is emitting x-ray pulses and the x-ray detector (6b) image data are readout, so allowing acquisition of multiple bi-dimensional views of the patient from different projection angles.

The acquired multiple bi-dimensional views data are fed to a processing algorithm performing tri-dimensional reconstruction of the volume associated with the selected region of interest.

Figure 5:
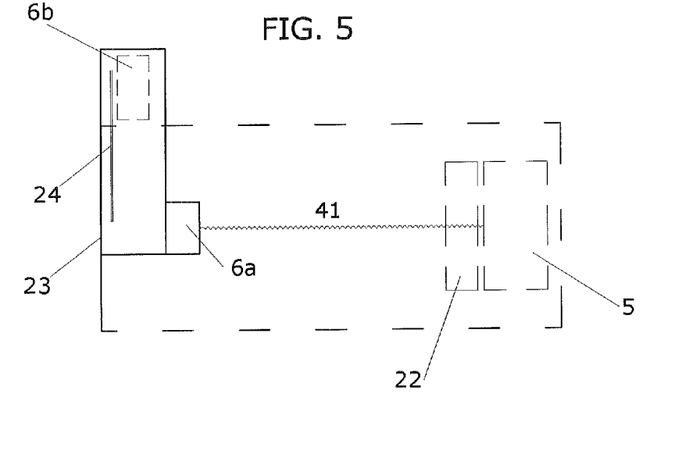
FIG. 5 illustrates the details of the panoramic imaging process.

With reference to FIG. 5, the details of the panoramic imaging process are illustrated.

When a panoramic imaging mode and a desired region of interest have been selected, the x-ray sensor cassette (23) is laterally slided by the horizontal motor drive (25), so that the panoramic x-ray detector (6a) is set in position for panoramic imaging, symmetrically aligned in the horizontal direction with respect to the central axis (41) of the x-ray beam.

The primary x-ray collimator (22) aperture is so adjusted that the x-ray beam has an elongated shape, having a narrow width and a height such as to exactly impinge on the active area of the panoramic x-ray detector (6a).

The patient is accurately positioned in between the x-ray generator (5) and the x-ray detector (6a), stabilized and aligned by the patient positioning system (7).

Under above conditions the rotating arm (3) starts a roto-translation scanning movement around the patient, while simultaneously the x-ray generator (5) is emitting x-rays and the x-ray detector (6a) image data are readout, so allowing acquisition and reconstruction of the bi-dimensional panoramic image.

The panoramic image reconstruction can occur according to profiles of combination of successive images, typically by shift and add; the combination profiles can be selected among pre-configured profiles, or can be adjustable by the user during post-processing, in order to optimize the enhancement of the layer in focus for particular anatomic regions of interest.

Figure 6A:
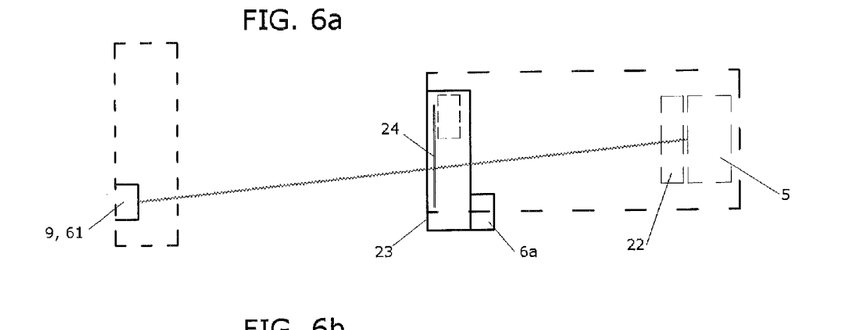
FIGS. 6a and 6b illustrates the details of the cephalometric imaging process.
Figure 6B:
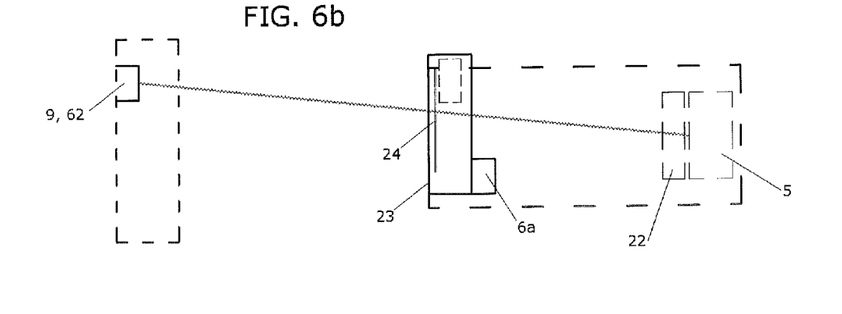

With reference to FIGS. 6a and 6b, the details of the cephalometric imaging process are illustrated.

When a cephalometric imaging mode and a desired region of interest have been selected, the x-ray sensor cassette (23) is laterally slided by the horizontal motor drive (25), so that the aperture of the secondary x-ray collimator (24) is set in a starting position for a cephalometric imaging process.

In this imaging mode the primary x-ray collimator (22) aperture is fixedly set to a rectangular size limiting a rectangular x-ray beam whose sectional dimensions in the plane of the secondary x-ray collimator (24) are fully contained within the same secondary collimator.

In other words the sectional height is slightly exceeding the upper and lower border of the secondary collimator aperture but internal to the upper and lower borders of the secondary collimator (24), while the sectional width is such large to remain contained in the secondary collimator (24) during the entire cephalometric scanning process but external to the starting and ending positions of the secondary collimator aperture (31).

The patient is accurately positioned in between the x-ray generator (5) and the cephalometric x-ray detector (9), stabilized and aligned by the cephalometric patient positioning system (10).

Under above conditions the x-ray sensor cassette (23) starts a linear scanning movement from a starting position to an end position, synchronized with the linear movement of the cephalometric x-ray detector (9) from a starting position (61) to an end position (62), while simultaneously the x-ray generator (5) is emitting x-rays and the cephalometric x-ray detector (9) image data are readout, so allowing acquisition and reconstruction of the bi-dimensional cephalometric image.

Figure 7:
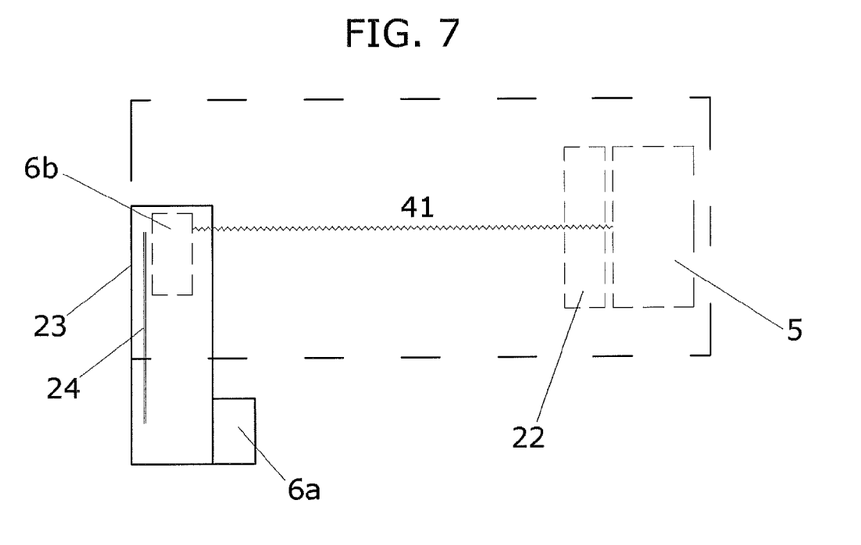
FIG. 7 illustrates the details of the CT imaging process in the extended view modality.

With reference to FIG. 7, the details of the CT imaging process in extended view modality are illustrated.

When a CT imaging mode in extended view and a desired region of interest have been selected, the x-ray sensor cassette (23) is laterally slided by the horizontal motor drive (25), so that the CT x-ray detector (6b) is set in position for CT imaging, asymmetrically aligned in the horizontal direction with respect to the central axis (41) of the x-ray beam.

Typically the CT detector will be aligned with a lateral offset about 25% of its width.

The primary x-ray collimator (22) aperture is so adjusted that the x-ray beam is rectangular shaped, having a width and height such as to exactly impinge on the active area of the CT x-ray detector (6b).

The patient is accurately positioned in between the x-ray generator (5) and the x-ray detector (6b), stabilized and aligned by the patient positioning system (7).

Under above conditions the rotating arm (3) starts a rotation around the patient, while simultaneously the x-ray generator (5) is emitting x-ray pulses and the x-ray detector (6b) image data are readout, so allowing acquisition of multiple bi-dimensional views of the patient from different projection angles.

The acquired multiple bi-dimensional views data are fed to a processing algorithm performing tri-dimensional reconstruction of the volume associated with the selected region of interest.

The exemplary apparatus described in the above mentioned embodiments finds useful industrial application in the field of dentistry, oral and maxilla-facial surgery and implantology, otolaryngology and other medical diagnostic radiographic examinations.

However the apparatus of the present invention is not limited to medical use, and can be advantageously applied in other non medical fields where multiple x-ray detectors and multiple radiographic imaging modes are required.

Finally it should be noted that throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds or groups described in conjunction with a particular aspect, embodiment or example of the invention are to be understood to be applicable to any other aspect, embodiment or example described herein unless incompatible therewith.

The invention claimed is:

1. A method for performing Digital Radiography according to multiple imaging modes, the method comprising the steps of:
   positioning an object between a radiation source and a x-ray detector using an object support and positioning system;
   selecting a radiographic imaging modality and a desired region of interest;

adjusting, by at least one of plural x-ray collimators, a shape of an x-ray beam according to the selected imaging modality;

positioning the X-ray detector in a predefined position into the X-ray beam;

generating X-ray radiation by the radiation source;

performing a movement for scanning of the object while detecting the X-ray radiation by means of the x-ray detector;

performing a readout of the x-ray detector image data, acquisition and elaboration in order to obtain a processed image or tridimensional data set of the selected region of interest according to the selected imaging modality, wherein in at least one said imaging modality the x-ray detector is a large area x-ray detector of rectangular dimensions which is enclosed within a x-ray sensor cassette, the x-ray sensor cassette is equipped with at least one motor drive providing horizontal movement transverse to a reference axis of the x-ray beam, the plural x-ray collimators include at least one secondary x-ray collimator utilized for cephalometric radiography and that is also enclosed within the x-ray sensor cassette, and the at least one secondary x-ray collimator is farther from the x-ray source than the large area x-ray detector is from the x-ray source.

2. The method according to claim 1, wherein the x-ray detector is detachably mounted on the x-ray sensor cassette on a side facing the x-ray source, for performing an imaging process according to a first said imaging modality.

3. The method according to claim 1, wherein the x-ray detector is equipped with mechanical and electrical release and can be manually detached and displaced back and forth from a first mount, for performing an imaging process according to a first said imaging modality, to a second mount, for performing an imaging process according to a second said imaging modality.

4. The method according to claim 3, wherein the first imaging modality is dental panoramic radiography and the second imaging modality is cephalometric radiography.

5. The method according to claim 1, wherein the selected imaging modality is computed tomography.

6. The method according to claim 1, wherein, prior to scanning movement and x-ray exposure, a primary one of the plural x-ray collimators is set to an elongated aperture producing a fan shaped x-ray beam, and the x-ray detector is moved to an exposure position horizontally symmetrically aligned into the x-ray beam by a horizontal transverse movement of the x-ray sensor cassette, for performing a dental panoramic imaging process.

7. The method according to claim 1, wherein, prior to scanning movement and x-ray exposure, a primary one of the plural x-ray collimators is set to a rectangular aperture producing a rectangular shaped x-ray beam, and the x-ray detector is moved to an exposure position horizontally symmetrically aligned into the x-ray beam by a horizontal transverse movement of the x-ray sensor cassette, for performing a computed tomography imaging process.

8. The method according to claim 1, wherein, prior to scanning movement and x-ray exposure, a primary one of the plural x-ray collimators is set to a rectangular aperture producing a rectangular shaped x-ray beam, and the x-ray detector is moved to an exposure position horizontally asymmetrically aligned into the x-ray beam by a horizontal transverse movement of the x-ray sensor cassette, for performing a computed tomography imaging process with extended view.

9. The method according to claim 1, wherein, prior to scanning movement and x-ray exposure, a primary one of the plural x-ray collimators is fixedly set to a rectangular aperture producing a rectangular shaped x-ray beam, the secondary x-ray collimator has a vertically elongated aperture producing a fan shaped x-ray beam and is moved to a starting position by a horizontal transverse movement of the x-ray sensor cassette, for performing a cephalometric imaging process.

10. The method according to claim 9, wherein the cephalometric imaging process is performed by a synchronized horizontal transverse movement of the x-ray sensor cassette, correspondingly moving the fan shaped x-ray beam produced by the aperture of the secondary x-ray collimator, and a cephalometric x-ray detector.

11. An apparatus for performing Digital Radiography according to multiple imaging modes, comprising:

means for positioning an object in between a radiation source and a x-ray detector;

means for selecting a radiographic imaging modality and a desired region of interest;

means for adjusting, by at least one of plural x-ray collimators, a shape of an x-ray beam according to a selected imaging modality;

means for positioning the X-ray detector in a predefined position into the X-ray beam;

means for generating X-ray radiation by a radiation source;

means for performing a combined movement of source and detector for scanning of the object while detecting the X-ray radiation by means of the x-ray detector;

means for performing a readout of the x-ray detector image data, acquisition and elaboration in order to obtain a processed image or tridimensional data set of the selected region of interest according to the selected imaging modality, wherein the x-ray detector is at least one large area x-ray detector of rectangular dimensions which is enclosed within a x-ray sensor cassette, the x-ray sensor cassette is equipped with at least one motor drive providing horizontal movement transverse to a reference axis of the x-ray beam, and the plural collimators include at least one secondary collimator configured for cephalometric radiography and that is also enclosed within the x-ray sensor cassette, and the at least one secondary collimator is farther from the x-ray source than the large area x-ray detector is from the x-ray source.

* * * * *